(12) United States Patent
Coates et al.

(10) Patent No.: US 6,475,574 B1
(45) Date of Patent: *Nov. 5, 2002

(54) DIREACTIVE MESOGENIC COMPOUNDS AND INTERMEDIATES

(75) Inventors: David Coates, Dorset (GB); Simon Greenfield, Dorset (GB)

(73) Assignee: Merck Patent Gesellschaft mit beschranhkter Haftung (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/575,801

(22) Filed: May 22, 2000

Related U.S. Application Data

(63) Continuation of application No. 08/875,767, filed as application No. PCT/EP96/00240 on Jan. 22, 1996, now Pat. No. 6,090,308.

(30) Foreign Application Priority Data

Feb. 6, 1995 (GB) .............................................. 9502294
Sep. 15, 1995 (EP) ............................................. 95114518

(51) Int. Cl.⁷ ....................... C09K 19/12; C09K 19/20; C09K 19/38; C07C 69/76; C08G 85/60
(52) U.S. Cl. .............. 428/1.1; 252/299.65; 252/299.66; 252/299.67; 560/66; 560/95; 526/72
(58) Field of Search ...................... 252/299.66, 299.67, 252/299.65; 428/1.1; 560/65, 59, 85, 95, 66; 526/72

(56) References Cited

U.S. PATENT DOCUMENTS

| | | | | |
|---|---|---|---|---|
| 5,210,630 A | * | 5/1993 | Heyderickx et al. | 359/106 |
| 5,401,437 A | * | 3/1995 | Im | 252/299.01 |
| 5,567,349 A | * | 10/1996 | Kelly et al. | 252/299.01 |
| 5,593,617 A | * | 1/1997 | Kelly et al. | 252/299.67 |
| 5,622,648 A | * | 4/1997 | Parri et al. | 252/299.66 |
| 5,641,426 A | * | 6/1997 | Nerad et al. | 252/299.01 |
| 5,723,066 A | * | 3/1998 | Coates et al. | 252/299.01 |
| 5,746,938 A | * | 5/1998 | Coates et al. | 252/299.01 |
| 5,833,880 A | * | 11/1998 | Siemens meyer et al. | 252/299.64 |
| 5,871,665 A | * | 2/1999 | Coates et al. | 252/299.01 |
| 6,042,745 A | * | 3/2000 | Coates et al. | 252/299.01 |
| 6,090,308 A | * | 7/2000 | Coates et al. | 252/299.65 |
| 6,187,222 B1 | * | 2/2001 | Coates et al. | 252/299.01 |

FOREIGN PATENT DOCUMENTS

| | | | |
|---|---|---|---|
| EP | 405713 | * | 1/1991 |
| WO | 93/22397 | * | 11/1993 |

* cited by examiner

*Primary Examiner*—Shean C. Wu
(74) *Attorney, Agent, or Firm*—Millen, White, Zelano & Branigan, P.C.

(57) ABSTRACT

The present invention generally relates to a direactive compound which is of the formula IV A

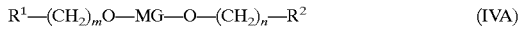

$$R^1-(CH_2)_mO-MG-O-(CH_2)_n-R^2 \qquad (IVA)$$

wherein $R^1$, $R^2$, m, n, and MG are defined herein.

16 Claims, No Drawings

DIREACTIVE MESOGENIC COMPOUNDS AND INTERMEDIATES

This application is a continuation of application Ser. No. 08/875,767 filed Aug. 5, 1997, now U.S. Pat. No. 6,090,308, which is a 371 of PCT/EP96/00240 filed Jan. 22, 1996.

The invention relates to direactive mesogenic compounds or mixtures thereof obtainable by a) treating a mesogenic diol of formula I,

HO—MG—OH     (I)

in which
MG is a mesogenic group,
with a mixture of the halides of formula II and III, $X^1$—$(CH_2)_m$—$R^a$     (II)

$X^2$—$(CH_2)_n$—$R^b$     (III)

in which
$X^1$ and $X^2$ are each independently Cl, Br or I,
m and n are different integers between 1 and 20
$R^a$ and $R^b$ are each independently groups selected from —$CH_2OH$ or —CH=CWH wherein
W is H, $CH_3$ or Cl,
in the presence of a base, and b) treating the resulting intermediate
- in the case of $R^a$ and $R^b$ being —$CH_2OH$, with a vinyl derivative of formula $CH_2$=CW—$(CO)_a$—O— or a reactive derivative thereof, in which a is 0 or 1
- in the case of $R^a$ and $R^b$ being —CH=CWH with a perbenzoic acid.

The invention furthermore relates to the preparation of such compounds and to their use in electrooptical scattering systems and for the preparation of oriented liquid crystal polymers.

Reactive liquid crystal compounds can be polymerized in situ, whilst in their liquid crystal phase, to give highly crosslinked anisotropic films which can be used, for example, as polarizing beam splitters (see, for example, EP 0,428,213). Reactive liquid crystal compounds have furthermore been proposed for electrooptical scattering systems (see, for example, EP 0,451,905), cholesteric polarizers (e.g. EP 0,606,940) and compensation films for STN displays (e.g. EP 0,423,881).

Reactive liquid crystal diesters of formula

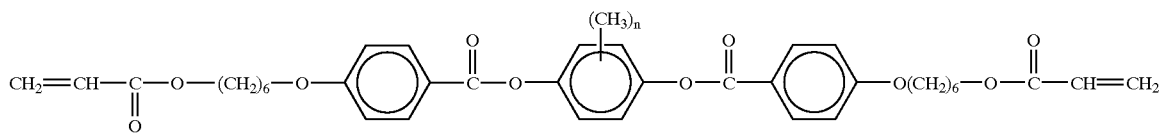

are mentioned in EP 0,261,712 (n=0), EP 0,331,233 (n=1). Reactive liquid crystal biphenyls of formula

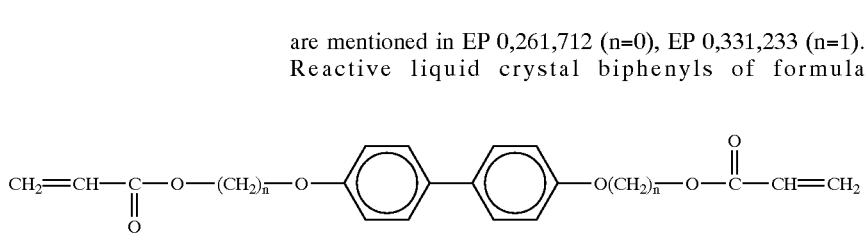

are disclosed by EP 0,405,713.

The International Patent application WO 93122397 discloses a compound of formula

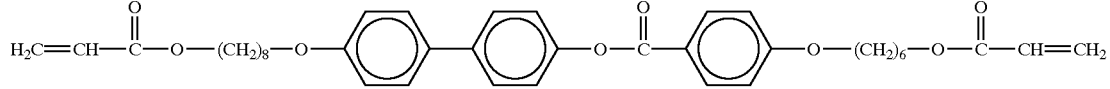

These reactive liquid crystalline compounds often exhibit, however, rather high melting points disadvantageous values of the birefringence and comparable narrow mesophase ranges.

In view of the broad range of applications of reactive liquid crystal compounds it was desirable to have available further compounds of this type which fulfill the various requirements such as a reasonably low melting point, a high birefringence, a broad mesogenic range and preferably an enantiotropic nematic range to a high degree.

It was an object of the present invention to provide new reactive liquid crystalline compounds with advantageous properties thus extending the pool of reactive liquid crystal compounds available to the expert. Other objects of the present invention can be taken from the following detailed specification.

The present invention thus relates to reactive mesogenic compounds or mixtures thereof obtainable by treating mesogenic diols of formula I, in particular those having a symmetric structure unit with a mixture of halides of formula II and III and to their use in electrooptical systems of scattering type and for the preparation of oriented liquid crystal polymers. The invention furthermore relates to the preparation of compounds according to formula I.

Preferred embodiments of the present invention are:

a) Composition of direactive compounds comprising at least one compound of each formula IV, V and VI, $$R^1-(CH_2)_m-O-MG-O-(CH_2)_n-R^2 \quad\quad IV$$

$$R^1-(CH_2)_m-O-MG-O-(CH_2)_m-R^1 \quad\quad V$$

$$R^2-(CH_2)_n-O-MG-O-(CH_2)_n-R^2 \quad\quad VI$$

in which MG, m and n have the meaning given, and $R^1$ and $R^2$ are each independently $$-CH_2-O-(CO)_a-CW=CH_2 \text{ or}$$

$$-\overset{O}{\overset{/\backslash}{CH-CHW}}.$$

b) Direactive compound or mixture thereof in which
   m—n>1, in particular 2, 3 or 4.
c) Direactive compound or mixture thereof in which MG is a mesogenic group of formula VIII, $$-(A^1-Z^1)_o-A^2- \quad\quad VIII$$

in which
A$^1$ and A$^2$ are each independently
(a) 1,4-phenylene in which one or two CH groups may be replaced by N;
(b) 1,4-cyclohexylene in which one or two non-adjacent CH$_2$ groups may be replaced by —O— or one —CH— group may be replaced by —C(CN)—;
(c) naphthaline-2,6-diyl;
it being possible that group (a) is substituted by halogen cyano or alkyl, alkoxy or alkanoyl with 1 to 6 C atoms,
Z$^1$ is each independently —COO—, —O—CO—, —CH$_2$—CH$_2$—, —C≡C—, —CH$_2$O—, —OCH$_2$— or a single bond, and
o is 1, 2 or 3.
d) Direactive compound or mixture thereof in which MG is selected from the structure elements (1) to (6).

(1) [phenyl-phenyl structure with (L)$_r$ substituents]

(2) [phenyl-COO-phenyl structure with (L)$_r$ substituents]

(3) [phenyl-phenyl-COO-phenyl structure with (L)$_r$ substituents]

(4) [phenyl-COO-phenyl-phenyl structure with (L)$_r$ substituents]

(5) [phenyl-COO-phenyl-OCO-phenyl structure with (L)$_r$ substituents]

(6) [phenyl-phenyl-phenyl structure with (L)$_r$ substituents]

in which
L is CH$_3$, Cl, F, OCH$_3$ or —CO—CH$_3$, and
r is 0, 1, 2 or 4.
e) Direactive compound or mixture thereof in which n and m are given by the following table:
m 5 5 5 4 4
n 2 3 4 2 3
A further aspect of the present invention is direactive compounds of formula IV A $$R^1-(CH_2)_mO-MG-O-(CH_2)_n-R^2 \quad\quad (IVA)$$

in which
R$^1$ and R$^2$ have the meaning given,
m and n are different integers between 2 and 10, and
MG is a mesogenic group, the core of which being symmetrical, preferably a structure element of formula (1), (5) or (6), in particular
direactive compounds of the formula IVA1

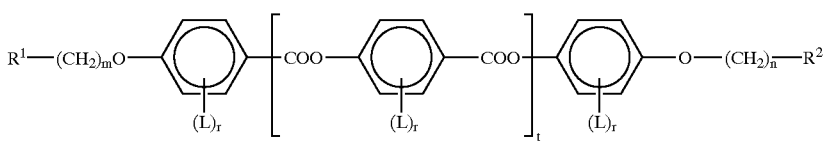

IVA1 in which
R¹, R²,
L and r have the meaning given,
m and n are different integers between 2 and 10, and t is 0 or 1.

Other aspect of the invention are the polymers prepared by polymerizing a monomer as described above and chemical intermediate compounds or mixtures thereof useful in preparing diireactive compounds or mixtures thereof as described above, comprising mesogene-containing molecules, said mesogenes having two side chains attached thereto that contain hydroxyl or vinyl group at the end thereof, said mesogenes and said functional groups being separated by at least two to twenty spacer atoms, wherein both spacer groups have different chain length.

Above and below, the term reactive mesogenic compounds refers to reactive rod-like molecules which may be enantiotropic, monotropic or isotropic, preferably, however, enantiotropic or monotropic.

In the inventive compounds in which MG is a mesogenic group of formula VIII, A¹ and A² can be independently from each other an unsubstituted or a substituted 1,4-phenylene group of formula

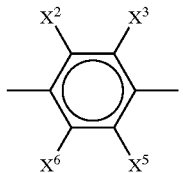

X², X³, X⁵ and X⁶ can be independently from each other H, F, Cl, methyl or CN.

In the following, for the sake of simplicity, the following notation will be used:

Phe. 2 X² 3 X³ 5 X⁵ 6 X⁶ is a 1,4-phenylene group carrying in 2-position the group X², in 3-position the group X³ etc.; in case X², X³, X⁵ and/or X⁶, denote H, this will not be specified in above notation, i.e. only true substitutions will be listed. Thus Phe, for example, is an unsubstituted 1,4-phenylene group while Phe.2F 5 Cl is a 2-fluoro-5-chloro-1,4-phenylene group. Furthermore, Pyr is pydmidine-2,5diyl, Pyd is pyrdine-2,5diyl and Nap is a naphthalene-2,6-diyl group. The notation Pyr and Pyd in each case include the 2 possible positional isomers.

The compounds according to formula IV comprise 2- and 3-ring compounds (n=1 or 2) of formulae IV2 and IV3:

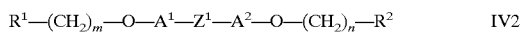    IV2

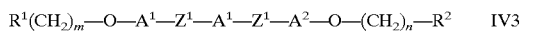    IV3

In the 3-ring compounds of formula IV3, the ring groups A¹ can be chosen independently from each other.

Especially preferred is a smaller group of 2-ring compounds exhibiting the following structures for —A¹—Z¹—A²—:

—Phe.2CH₃—Phe— IV2-1
—Phe.3CH₃—Phe— IV2-2
—Phe.2Cl—Phe— IV2-3
—Phe.3Cl—Phe— IV2-4
—Phe.2CN—Phe— IV2-5
—Phe.3CN—Phe— IV2-6
—Phe.2Cl3Cl—Phe— IV2-7
—Phe.2Cl3F—Phe— IV2-8
—Phe.2F—Phe— IV2-9
—Phe.3F—Phe— IV2-10
—Phe.—Phe— IV2-11
—Phe.F—Nap— IV2-12
—Phe.2Cl—Nap— IV2-13
—Phe.F—Nap— IV2-14
—Phe.3Cl—Nap— IV2-15
—Phe.2F—Pyr— IV2-16
—Phe.2F—Pyr— IV2-17
—Phe.2CH₃—Pyd— IV2-18
—Phe.2Cl—Pyd— IV2-19
—Phe.F—CH₂CH₂—Phe— IV2-20
—Phe.3F—CH₂CH₂—Phe— IV2-21
—Phe.2Cl—CH₂CH₂—Phe— IV2-22
—Phe.3Cl—CH₂CH₂—Phe— IV2-23
—Phe.2CN—CH₂CH₂—Phe— IV2-24
—Phe.3CN—CH₂CH₂—Phe— IV2-25
—Phe.2Cl3Cl—CH₂CH₂—Phe— IV2-26
—Phe.2Cl3F—CH₂CH₂—Phe— IV2-27

The 3-ring compounds according to formula IV3 preferably exhibit the following structures for —A¹—Z¹—A¹—Z¹—A²:

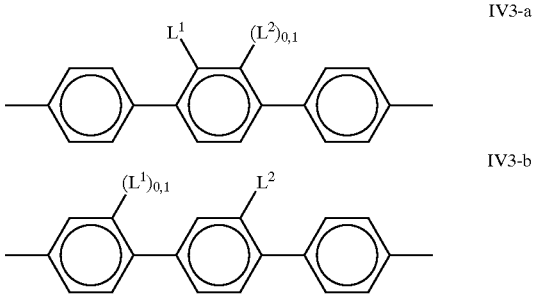

-continued

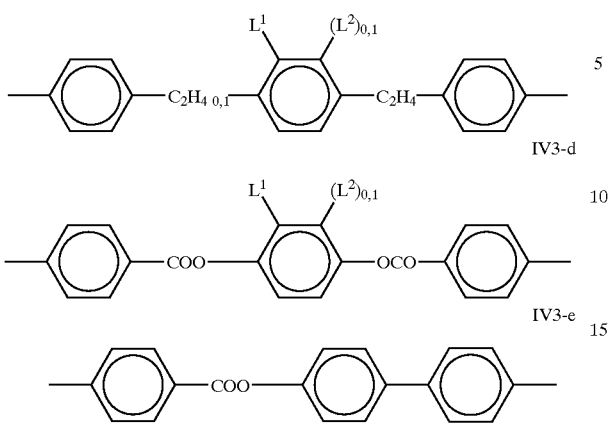

In these structures, IV3-a to IV3-d, $L^1$ and $L^2$ denote independently from each other H, —Cl, —F, —CN and $C_nH_{2r+1-s}$ and, in particular, —Cl, —F, —CN, —$CH_3$, and/or —$C_2H_5$.

Especially preferred are the following patterns:

—Phe—Phe.2CH$_3$—Phe— IV3-a-1
—Phe—Phe.2Cl—Phe— IV3-a-2
—Phe—Phe.2CN—Phe— IV3-a-3
—Phe—Phe.2F—Phe— IV3-a-4
—Phe—Phe—Phe— IV3-a-5
—Phe—Phe.2C$_2$H$_5$—Phe— IV3-a-6
—Phe—Phe.3CH$_3$—Phe— IV3-b-1
—Phe—Phe.3Cl—Phe— IV3-b-2
—Phe—Phe.3CN—Phe— IV3-b-3
—Phe—Phe.3C—Phe— IV3-b-4
—Phe—Phe.3C$_2$H$_5$— IV3-b-5
—Phe.3F—Phe.3Cl—Phe— IV3-b-6
—Phe.3F—Phe.3CH$_3$—Phe— IV3-b-7
—Phe.3Cl—Phe.3Cl—Phe— IV3-b-8
—Phe.3Cl—Phe.3CH$_3$—Phe— IV3-b-9
—Phe—Phe.2Cl—Phe.3Cl— IV3-b-10
—Phe—Phe.3Cl—Phe.3Cl— IV3-b-11
—Phe—Phe.2Cl—Phe.2Cl— IV3-b-12
—Phe—Phe.3Cl—Phe.2Cl— IV3-b-13
—Phe—Phe.2CH$_3$—Phe.3Cl— IV3-b-14
—Phe—Phe.3CH$_3$—Phe.3Cl— IV3-b-15
—Phe—Phe.2CH$_3$—Phe.2Cl— IV3-b-16
—Phe—Phe.3CH$_3$—Phe.2Cl— IV3-b-17
—Phe—Phe.2F—Phe.3Cl— IV3-b-18
—Phe—Phe.3F—Phe.3Cl— IV3-b-19
—Phe—Phe.2F—Phe.2Cl— IV3-b-20
—Phe—Phe.3F.Phe.2Cl—V3-b-21
—Phe—Phe.2Cl—Phe.3CN— IV3-b-22
—Phe—Phe.3Cl—Phe.3CN— IV3-b-23
—Phe—Phe.2Cl—Phe.2CN— IV3-b-24
—Phe—Phe.3Cl—Phe.2CN— IV3-b-25
—Phe—Phe.2CH$_3$—Phe.3CN— IV3-b-26
—Phe—Phe.3CH$_3$—Phe.3CN— IV3-b-27
—Phe—Phe.2CH$_3$—Phe.2CN— IV3-b-28
—Phe—Phe.3CH$_3$—Phe.2CN— IV3-b-29
—Phe—Phe.3F—Phe.3CN— IV3-b-30
—Phe—Phe.2F—Phe.3CN— IV3-b-31
—Phe—Phe.3F—Phe.2CN— IV3-b-32
—Phe—Phe.2F—Phe.2CN— IV3-b-33
—Phe—Phe.2F—Phe.2F— IV3-b-34
—Phe—Phe.3F—Phe.3F— IV3-b-35
—Phe—Phe.2CH—C$_2$H$_4$Phe— IV3c-1
—Phe—Phe.2Cl—C$_2$H$_4$—Phe— IV3-c-2
—Phe—Phe.2CN—C$_2$H$_4$Phe— IV3-c-3
—Phe—Phe.2F—C$_2$H$_4$—Phe— IV3-c-4
—Phe—Phe.2C$_2$H$_5$—C$_2$H$_4$—Phe— IV3-c-5
—Phe—Phe.2Cl3F—C$_2$H$_4$—Phe— IV3c-6
—Phe—Phe.2Cl3ClC$_2$H$_4$—Phe— IV3-c-7
—Phe—C$_2$H$_4$—Phe.5CH$_3$—C$_2$H$_4$Phe— IV3-c-8
—Phe—C$_2$H$_4$—Phe.2Cl—C$_2$H$_4$—Phe— IV3-c-9
—Phe—C$_2$H$_4$—Phe.2CN—C$_2$H$_4$—Phe— IV3-c-10
—Phe—C$_2$H$_4$—Phe.F—C$_2$H$_4$—Phe— IV3-c-11
—Phe—C$_2$H$_4$—Phe.2OCF$_3$—C$_2$H$_4$—Phe— IV3-c-12
—Phe—COO—Phe.OCO—Phe— IV3-d-1
—Phe—COO—Phe.2CH$_3$—OCO—Phe— IV3-d-2
Phe—COO—Phe.3CH$_3$—OCO—Phe— IV3-d-3
—Phe—COO—Phe.2CH$_3$3CH$_3$—OCO—Phe— IV3-d-4
—Phe—COO—Phe.2OCH$_3$—OCO—Phe— IV3-d-5
—Phe—COO—Phe.2Cl—OCO—Phe— IV3-d-6
—Phe—COO—Phe.2F—OCO—Phe— IV3-d-7
—Phe—COO—Phe.2F3F—OCO—Phe— IV3-d-8
—Phe—COO—PhePhe— IV3-e-1
—Phe—COO—Phe.2FPhe— IV3-e-2
—Phe—COO—Phe.3FPhe— IV3-e-3
—Phe—COO—PhePhe.2F— IV3-e-4
—Phe—COO—PhePhe.3F— IV3-e-5
—Phe.2F—COO—PhePhe— IV3-e-6
—Phe.3F—COO—PhePhe— IV3-e-7

It was observed that the stability of 3-ring compounds wherein one of the 2 groups $Z^1$ is —COO— or —OCO— while the other denotes a single bond, can be increased if the compound is laterally di- or higher substituted, particularly di-substituted by —Cl, —F, —CN and/or —$CH_3$. Compounds of this type are preferred.

Especially preferred are further 3-ring compounds where both groups $Z^1$ are either —COO—, or —OCO— and at least one of the rings $A^1$, $A^{1'}$ and $A^2$ are at least mono substituted.

In the compounds of formula IV $R^1$ is $CH_2$=CW—COO—$CH_2$—, $CH_2$=CH—O—$CH_2$—,

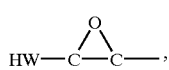

with W being H, Cl or alkyl with 1–5 C atoms and m being 1–7.

Preferably, $R^1$ and $R^2$ is a vinyl group, an acrylate group, an epoxy group and especially preferred are the following means of $R^1$ and $R^2$:

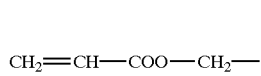  $R^1$-1

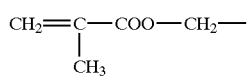  $R^1$-2

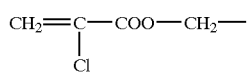  $R^1$-3

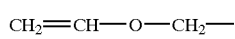  $R^1$-4

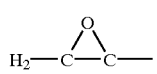  $R^1$-5 with alkyl denoting $C_1$–$C_3$-alkyl and m being 1–5.

The reaction methods mentioned are briefly summarized in the following synthetic tree:

Scheme I

HO—MG—OH

+
Mixture of
Br—$(CH_2)_{\overline{m}}$—OH/
Br—$(CH_2)_{\overline{n}}$—OH
Butanone, $K_2CO_3$, heat

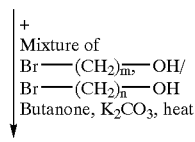

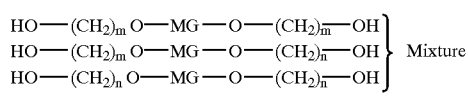 } Mixture

| Butylvinyl ether | |
| DCM | Mixture of |
| 1,10-Phenanthroline | "diacrylates" |
| Pd (II)-Acetate | |

Mixture of
"Divinylethers"

DCM = dichloromethane

Scheme II

HO—MG—OH

Mixture of
Br—$(CH_2)_{\overline{m}}$—CH=$CH_2$
Br—$(CH_2)_{\overline{n}}$—CH=$CH_2$
butanone, $K_2CO_3$, heat

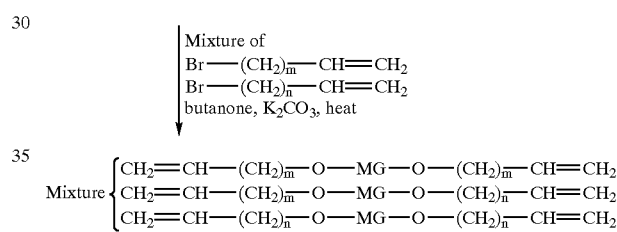

Scheme III

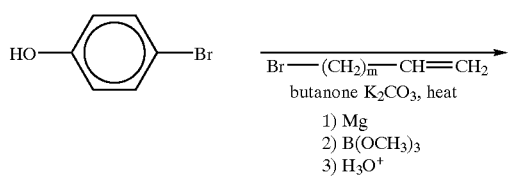

1) Mg
2) $B(OCH_3)_3$
3) $H_3O^+$

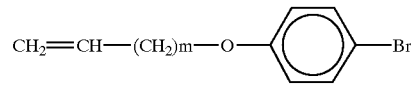

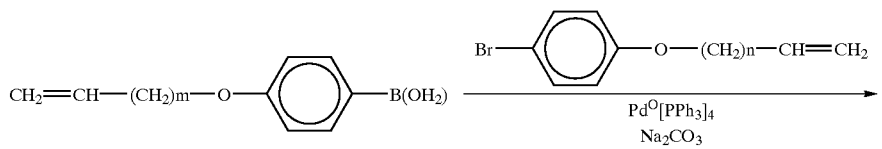

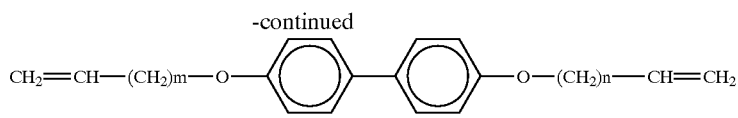
Certain compounds or mixtures according to the invention are obtainable in a "one-pot-synthesis" as outlined in scheme IV:
Scheme IV
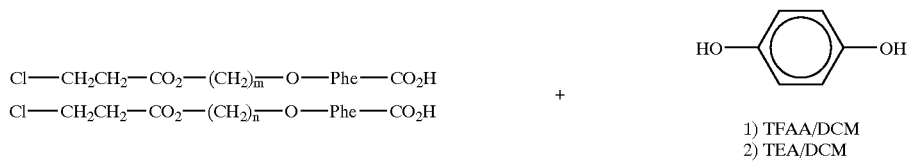
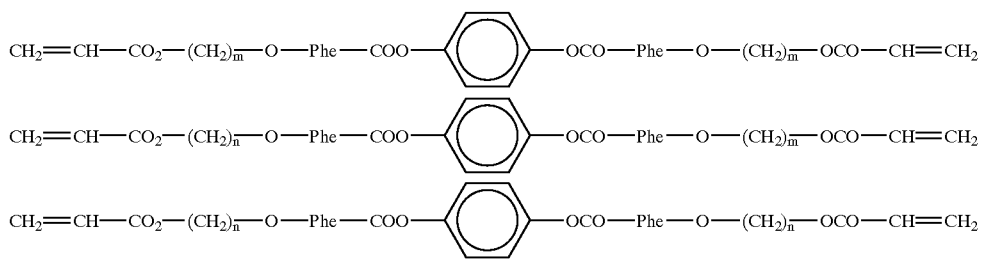
TFAA = trifluoroacetic acid
TEA = triethylamine
Individual compounds of this type can be obtained according to schemes V to VII:
Scheme V
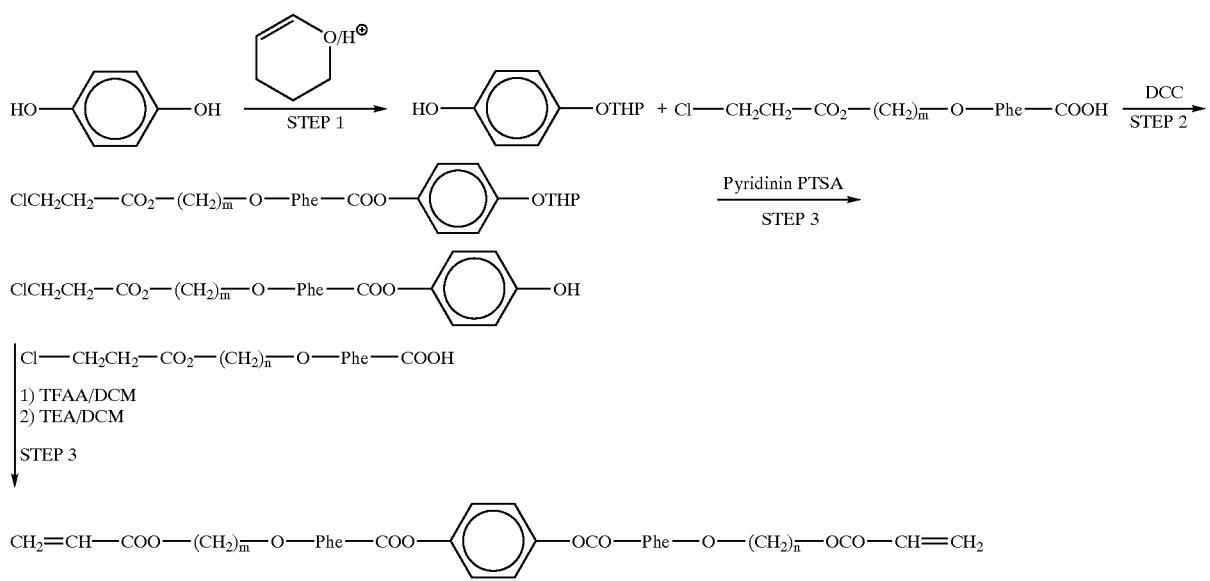
PTSA = p-toluenesulfonate Scheme VI
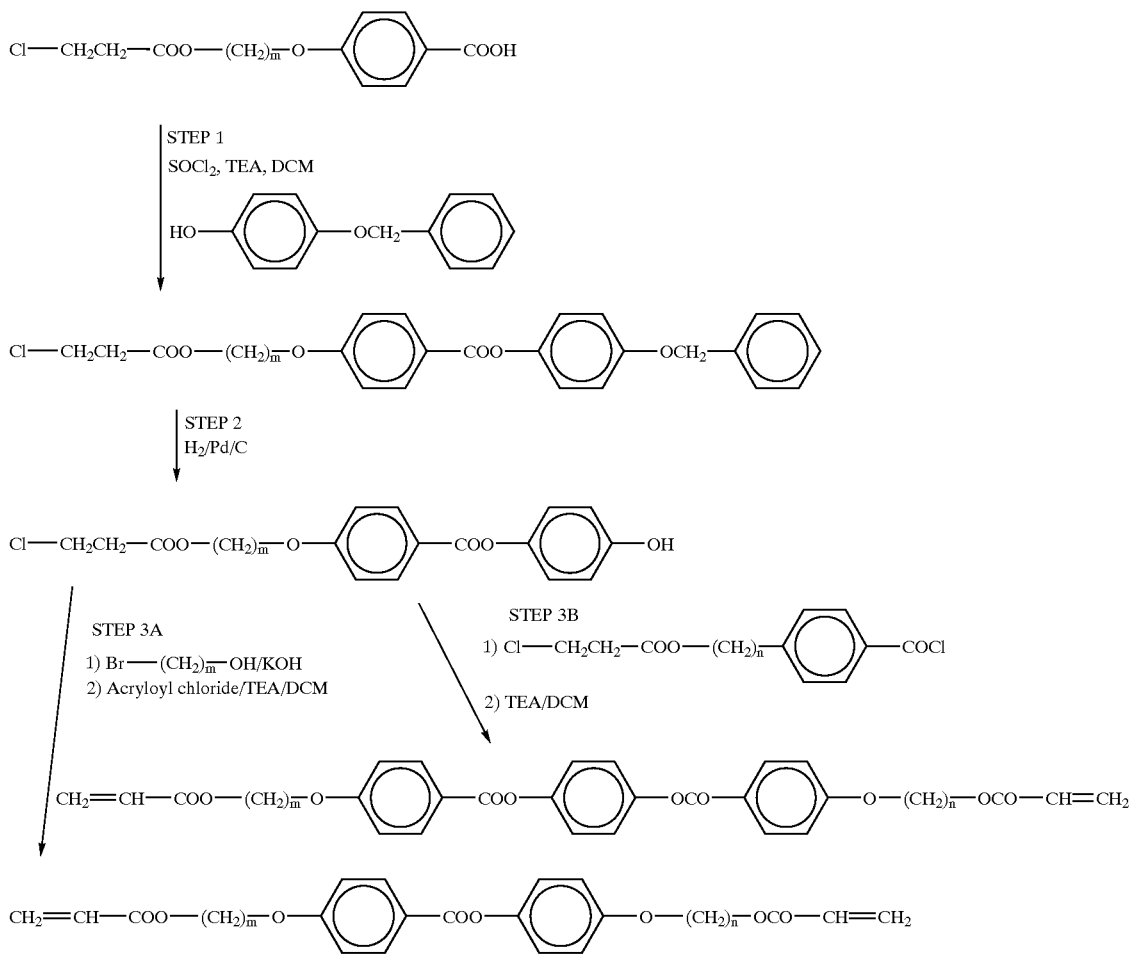
Scheme VII
(obtained according to WO 93/22397)
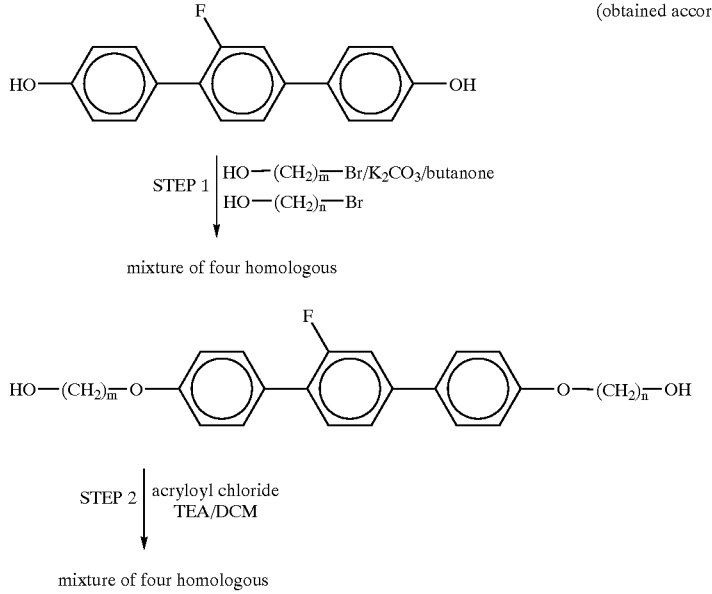
mixture of four homologous
mixture of four homologous

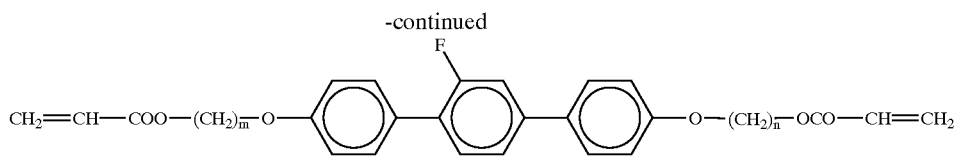

The reaction schemes mentioned above are to illustrate the invention without restricting it. The expert can choose other reaction methods without any inventive efforts.

In the following and ink the preceding, all percentages given are percentages by weight. Temperatures are given in degrees Celsius.

The following examples are intended to illustrate the invention without restricting it.

EXAMPLE 1

The reactive liquid crystalline compound (1)

is prepared via the sequence of reaction steps shown in scheme V. In step 4 of scheme V 2.2 moles TFM are added dropwise to a solution 2 moles of the phenol obtained in step 3 of scheme V and 2 moles of the benzoic acid in 2 l of DCM.

The reaction mixture is stirred at room temperature for 16 hours. Then 5 moles of TEA in 1 l of DCM are added. The mixture is stirred for 16 hours. Aqueous work-up and column chromatography give (1) which shows K 111 S.

The following compounds are obtained analogously:

| Compound No. | m | n | phase transition temperatures (° C.) |
|---|---|---|---|
| (2) | 3 | 5 | K 76 N 160 I |
| (3) | 4 | 5 | K 67 N 165 I |
| (4) | 4 | 6 | K 78 S 82 N 159 I |
| (5) | 5 | 6 | K 78 S 80 N 162 I |
| Comp 1 | 4 | 4 | K 105 N 164 I |
| Comp 2 | 5 | 5 | K 91 N 167 I |
| Comp 3 | 6 | 6 | K 105 (S 95) 152 I |

EXAMPLE 2

A mixture of 1 mol

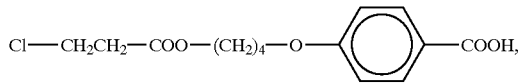

1 mol

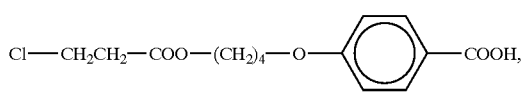

and 1 mol p-hydroquinone is treated with 22 moles of TFAA followed by 2.5 moles of TEA.

A mixture consisting of 1 part comp 1 and 1 part comp 3 and 2 parts of Compound No. (4) is obtained which shows a melting point of 56° C. and a clearing point of 163° C.

Analogously a mixture of the following compounds is obtained:

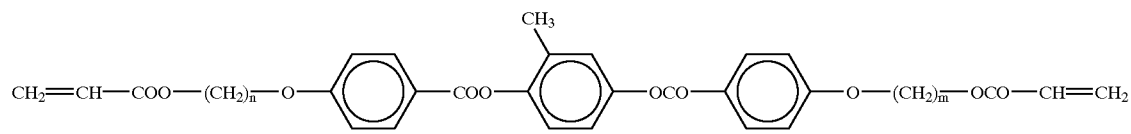

| n | m | parts |
|---|---|---|
| 3 | 3 | 1 |
| 6 | 6 | 1 |
| 3 | 6 | 1 |
| 6 | 3 | 1 |

This composition shows a melting point below 30° C. and a clearing point of 119° C.

EXAMPLE 3

A mixture of 0.5 moles of biphenol, 1.3 moles of potassium hydroxide, 0.6 moles of 3-bromopropanol and 0.6 moles of 3 bromohexanol is heated in 2 liters of butanone for 16 hrs. After aqueous work-up a mixture of 1 part of

HO—(CH$_2$)$_3$—O—⟨⟩—⟨⟩—O—(CH$_2$)$_3$—OH 1 part of

HO—(CH$_2$)$_6$—O—⟨⟩—⟨⟩—O—(CH$_2$)$_6$—OH, and 2 parts of

HO—(CH$_2$)$_6$—O—⟨⟩—⟨⟩—O—(CH$_2$)$_3$—OH is obtained.

This mixture is treated with 1.2 moles of acryloyl chloride and 1.2 moles of TEA in 1.5 liters of dichloroethane DCM and refluxed for 3 hours.

After aqueous work-up the resulting reaction mixture is purified by column-chromatography to yield a mixture of diacrylates (6), (7) and (8).

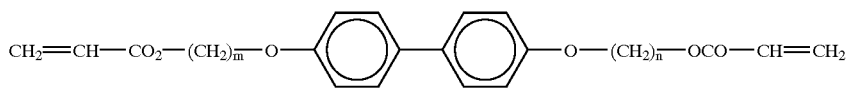

| Compound No. | m | n | parts |
|---|---|---|---|
| (6) | 3 | 3 | 1 |
| (7) | 5 | 6 | 1 |
| (8) | 3 | 6 | 2 |

Analogously a mixture of compounds of formulae (9), (10), (11) and (12) is obtained

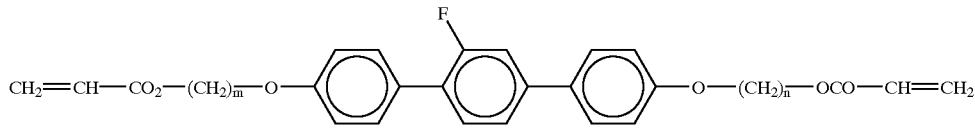

| Compound No. | m | n | parts |
|---|---|---|---|
| (9) | 3 | 3 | 1 |
| (10) | 6 | 6 | 1 |
| (11) | 3 | 6 | 1 |
| (12) | 6 | 3 | 1 |

What is claimed is:

1. A direactive compound which is of the formula IV A $$R^1-(CH_2)_mO-MG-O-(CH_2)_n-R^2 \qquad (IVA)$$

in which $R^1$ and $R^2$ are each independently

—CH$_2$—O—(CO)$_a$—CW=CH$_2$ or

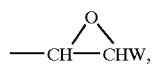

a is 0 or 1;
W is H, CH$_3$, or Cl;
m and n are different integers from 2 to 10, and
MG is a mesogenic group selected from:

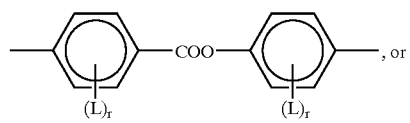  (2)

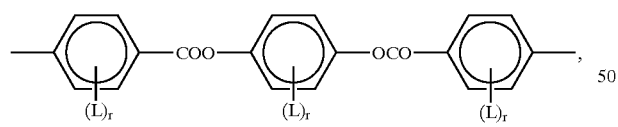  (5)

wherein L is
CH$_3$, Cl, F, OCH$_3$, or —CO—CH$_3$ and r is 0, 1, 2 or 4.

2. A direactive compound of the formula:

$$R^1-(CH_2)_mO-MG-O-(CH_2)_n-R^2$$

in which $R^1$ and $R^2$ are each independently

—CH$_2$—O—(CO)$_a$—CW=CH$_2$ or

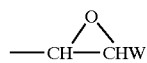

a is 0 or 1;
W is H, CH$_3$, or Cl;
m and n are different integers from 2 to 10, and MG is a mesogenic group of formula VIII, $$-(A^1-Z^1)_o-A^2- \qquad VIII$$

in which
$A^1$ and $A^2$ are each independently
(a) 1,4-phenylene in which one or two CH groups may be replaced by N;
(b) 1,4-cyclohexylene in which one or two non-adjacent CH$_2$ groups may be replaced by —O— or one —CH— group may be replaced by —C(CN)—;
(c) naphthaline-2,6-diyl;
wherein optionally the (a) group is substituted by halogen, cyano or alkyl with 1 to 6 C atoms,
$Z^1$ is each independently —COO—, —O—CO—, —CH$_2$—CH$_2$—, —C≡C—, —CH$_2$O—, —OCH$_2$— or a single bond, and
o is 1, 2 or 3; and MG is not a mesogenic group of formulae (1), (3), (4), or (6):

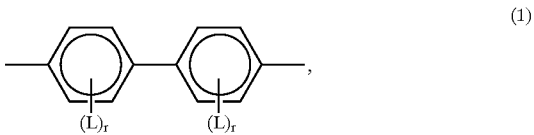  (1)

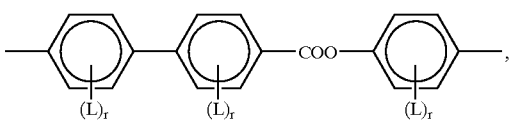  (3)

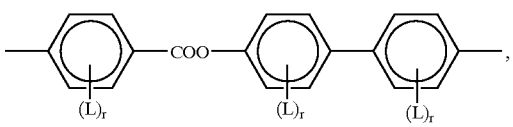  (4)

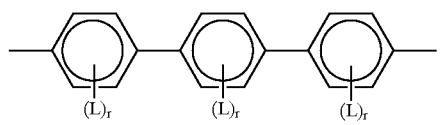 (6)

wherein

L is $CH_3$, Cl, F, $OCH_3$, or —CO—$CH_3$, and is 0, 1, 2 or 4.

3. A direactive compound according to claim 1, in which n and m are given by the following table:

m 5 5 5 4 4
n 2 3 4 2 3.

4. A direactive compound of the formula:

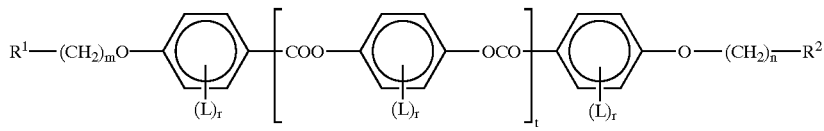

in which
$R^1$ and $R^2$ are each independently

—$CH_2$—O—(CO)$_a$CW=$CH_2$ or

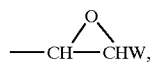

a is 0 or 1;
W is H, $CH_3$, or Cl;
wherein L is $CH_3$, Cl, F, $OCH_3$, or —CO—$CH_3$ and r is 0, 1, 2 or 4
m and n are different integers from 2 to 10, and
t is 1.

5. A polymer obtained by polymerizing a compound according to claim 1.

6. A polymer obtained by polymerizing a compound according to claim 1 which is an oriented liquid crystalline polymer.

7. An electrooptical scattering system which contains an oriented liquid crystalline polymer according to claim 6.

8. A direactive compound according to claim 2, wherein at least one MG group is a three ring group wherein one of the two $Z^1$ groups is —COO— or —OCO—, the other is a single bond and there are at least two lateral —Cl, —F, —CN or —$CH_3$ ring substituents.

9. A polymer obtained by polymerizing a compound according to claim 2 which is an oriented liquid crystalline polymer.

10. An electrooptical scattering system which contains an oriented liquid crystalline polymer according to claim 9.

11. A polymer obtained by polymerizing a compound according to claim 4 which is an oriented liquid crystalline polymer.

12. An electrooptical scattering system which contains an oriented liquid crystalline polymer according to claim 11.

13. A direactive compound according to claim 1 of formula:

wherein m=3 and n=4; m=3 and n=5; m4 and n=5; m=4 and n=6; or m=5 and n=6.

14. A direactive compound according to claim 1 of formula:

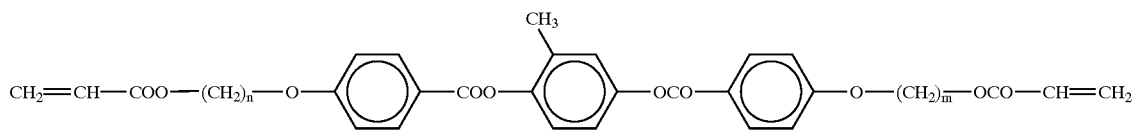

wherein m=6 and n=3; or m=3 and n=6.

15. A direactive mesogenic compound of claim 1, made by:
a) treating a mesogenic diol of formula I,

HO—MG—OH  (I)

with a mixture of the halides of formulae II and III, $X^1$—(CH$_2$)$_m$—R$^a$  (II)

$X^2$—(CH$_2$)$_n$—R$^b$  (III)

in the presence of a base, in which MG is a mesogenic group of formulae (2) or (5);
$X^1$ and $X^2$ are each independently Cl, Br or I,
m and n are different integers from 1 to 20, and
$R^a$ and $R^b$ are each independently groups selected from —CH$_2$OH or —CH=CWH wherein
W is H, CH$_3$ or Cl, and
b) treating the resulting intermediate
in the case of $R^a$ and $R^b$ being —CH$_2$OH, with a vinyl derivative of formula CH$_2$=CW—(CO)$_a$—O— or a reactive derivative thereof, in which a is 0 or 1; or
in the case of $R^a$ and $R^b$ being —CH=CWH with a perbenzoic acid.

16. A direactive mesogenic compound made by:
c) treating a mesogenic diol of formula I,

HO—MG—OH    (I)

with a mixture of the halides of formulae II and III, $X^1$—(CH$_2$)$_m$R$^a$    (II)

$X^2$—(CH$_2$)$_n$R$^b$    (III)

in the presence of a base,
in which MG is a mesogenic group
$X^1$ and $X^2$ are each independently Cl, Br or I,
m and n are different integers from 1 to 20, and
$R^a$ and $R^b$ are each independently groups selected from —CH$_2$OH or —CH=CWH wherein
W is H, CH$_3$ or Cl; and
the mesogenic group of the direactive mesogenic compound is not a mesogenic group of:

    (1)

    (3)

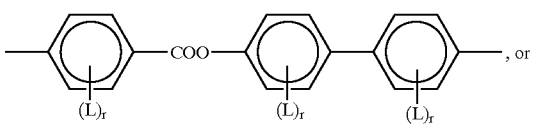    (4)

, or

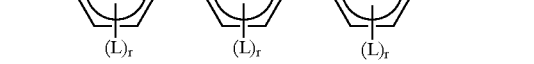    (6)

wherein:
L is CH$_3$, Cl, OCH$_3$, and
r is 0, 1, 2 or 4.

* * * * *

UNITED STATES PATENT AND TRADEMARK OFFICE
CERTIFICATE OF CORRECTION

PATENT NO. : 6,475,574 B1
DATED : November 5, 2002
INVENTOR(S) : David Coates et al.

It is certified that error appears in the above-identified patent and that said Letters Patent is hereby corrected as shown below:

Column 21,
Line 12, reads "is 0," should read -- r is 0, --

Column 22,
Line 28, reads "m4 and n=5" should read -- m=4 and n=5 --

Column 24,
Line 30, reads "CH3, Cl, OCH3, and" should read -- CH3, Cl, F, OCH3, or -CO-CH3, and --

Signed and Sealed this

Sixteenth Day of September, 2003

JAMES E. ROGAN
*Director of the United States Patent and Trademark Office*